(12) United States Patent
Luo et al.

(10) Patent No.: US 12,130,346 B2
(45) Date of Patent: Oct. 29, 2024

(54) NUCLEAR MAGNETIC RESONANCE (NMR) MEASUREMENT SYSTEM FOR NON-INVASIVE QUANTITATIVE DETECTION OF ORGANS

(71) Applicant: WUXI MARVEL STONE HEALTHCARE CO., LTD., Wuxi (CN)

(72) Inventors: Hai Luo, Chengdu (CN); Weiqian Wang, Chengdu (CN); Xiao Chen, Chengdu (CN); Yue Zhao, Chengdu (CN); Yunhao Xie, Chengdu (CN); Ziyue Wu, Chengdu (CN)

(73) Assignee: WUXI MARVEL STONE HEALTHCARE CO., LTD., Wuxi (CN)

(*) Notice: Subject to any disclaimer, the term of this patent is extended or adjusted under 35 U.S.C. 154(b) by 356 days.

(21) Appl. No.: 17/792,408

(22) PCT Filed: May 13, 2021

(86) PCT No.: PCT/CN2021/093488
§ 371 (c)(1),
(2) Date: Jul. 13, 2022

(87) PCT Pub. No.: WO2022/205575
PCT Pub. Date: Oct. 6, 2022

(65) Prior Publication Data
US 2023/0341491 A1 Oct. 26, 2023

(30) Foreign Application Priority Data
Mar. 31, 2021 (CN) .......................... 202110351077.3

(51) Int. Cl.
G01R 33/48 (2006.01)
A61B 5/055 (2006.01)
(Continued)

(52) U.S. Cl.
CPC .......... *G01R 33/4828* (2013.01); *A61B 5/055* (2013.01); *G01R 33/34092* (2013.01); *G01R 33/56563* (2013.01); *A61B 5/704* (2013.01)

(58) Field of Classification Search
CPC .................. A61B 5/055; A61B 5/4244; G01R 33/34092; G01R 33/4616; G01R 33/4838; G01R 33/4828
See application file for complete search history.

(56) References Cited

U.S. PATENT DOCUMENTS

2005/0021019 A1* 1/2005 Hashimshony ........ A61B 5/053
606/32
2006/0084861 A1 4/2006 Blank et al.
(Continued)

FOREIGN PATENT DOCUMENTS

CN 108209918 A 6/2018
CN 110780248 A * 2/2020 ............. A61B 5/055
(Continued)

Primary Examiner — Angela M Hoffa
Assistant Examiner — Younhee Choi
(74) Attorney, Agent, or Firm — Bayramoglu Law Offices LLC

(57) ABSTRACT

A comprehensive and integrated solution, including a dedicated system structure and grounding mechanism, a main radio frequency (RF) coil to transmit and receive signal, secondary RF coils to saturate unwanted signals from non-region-of-interest (ROI) in the excited region, an RF shielding structure configured to shield the main RF coil from generating signals on the non-ROI, and an environmental noise active cancellation mechanism is proposed to construct an NMR system for non-invasive quantitative detection of organs, and further improves the target region selectivity and detection accuracy.

10 Claims, 10 Drawing Sheets

(51) Int. Cl.
   *G01R 33/34*    (2006.01)
   *G01R 33/565*   (2006.01)
   *A61B 5/00*     (2006.01)

(56) References Cited

U.S. PATENT DOCUMENTS

2014/0232403 A1* 8/2014 Perkins .............. G01R 33/4828
                                                    324/309
2018/0220949 A1* 8/2018 Prado ................ G01R 33/4828

FOREIGN PATENT DOCUMENTS

| JP | 2005270422 A | 10/2005 |
| JP | 2008142479 A | 6/2008 |

\* cited by examiner

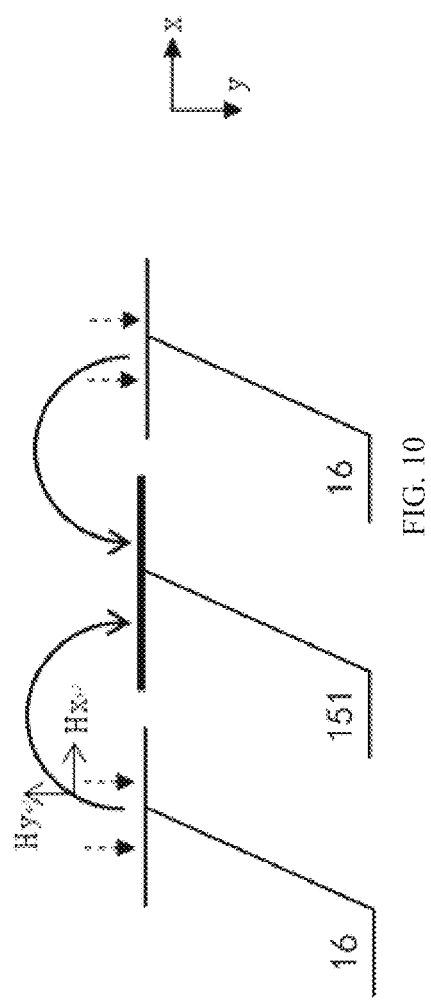

NUCLEAR MAGNETIC RESONANCE (NMR) MEASUREMENT SYSTEM FOR NON-INVASIVE QUANTITATIVE DETECTION OF ORGANS

CROSS REFERENCE TO THE RELATED APPLICATIONS

This application is the national phase entry of International Application No. PCT/CN2021/093488, filed on May 13, 2021, which is based upon and claims priority to Chinese Patent Application No. 202110351077.3, filed on Mar. 31, 2021, the entire contents of which are incorporated herein by reference.

TECHNICAL FIELD

The present disclosure relates to the technical field of nuclear magnetic resonance (NMR), and in particular, to an NMR measurement system for non-invasive quantitative detection of organs.

BACKGROUND

Traditional medical equipment mainly adopts such technical means as ultrasonic detection, NMR detection, and puncture detection to perform human organ detection (such as liver detection). However, the technical means have respective limitations. For example: (a) ultrasonic detection: traditional ultrasonic detectors can only perform qualitative detection, and cannot meet detection requirements when a fat content is less than or equal to 30%. The other type of ultrasound-based quantitative detection products for fatty liver and liver fibrosis have the main limitation in that the detection can be easily affected by insufficient ultrasonic penetration, and the success rate is low in detection in obese patients. (b) NMR detection: the magnetic resonance Dixon technique can be used to quantify fat, and the magnetic resonance elastography (MRE) technique can be used to measure liver fibrosis, which has a high cost in spite of meeting the requirements of detection accuracy. It usually takes about 5 million RMB or more for hospitals to obtain this technique, and the cost of a single test, for example, in Jiangsu is about 3,000 RMB, which is a high cost and cannot be widely used for fatty liver monitoring in early and middle stages. (c) Puncture detection (such as liver puncture detection): the detection means has high accuracy and is the gold standard for clinical detection, but it is extremely harmful to the human body. It is only suitable for absolutely necessary situations and cannot be widely used. In addition, it has extremely high requirements for sample extraction and technician operation.

The prior patent CN201911101865.6 "Method for non-invasive quantitative detection of organ fat based on magnetic resonance principle" discloses a non-invasive detection technique of organ fat based on a single-sided magnet NMR system. As shown in FIG. 1, the technique uses an external computer (that is, a computer device consisting of a display and a data processor), a radio frequency (RF) subsystem, and a portable single-sided permanent magnet module to construct a system for non-invasive quantitative detection of organ fat based on low-field NMR (LF-NMR), which has the advantages of portability and low cost, and enables non-invasive and safe quantitative detection of organ fat. However, due to the use of a single-sided permanent magnet, the magnetic field is extremely non-uniform, resulting in an excitation region as an irregular surface. FIG. 2 is an exemplary simulation diagram of an excitation region of a single-sided magnet NMR system. The excitation region is approximately saddle-shaped, with poor selectivity and limited excitation depth. This excitation region may not fall completely on to-be-detected organs. For example, in the saddle-shaped excitation region, a lower region may excite the subcutaneous fat layer, while its upper region may excite organs other than the liver, resulting in detection errors.

Therefore, in view of a non-ideal excitation region of the single-sided magnet NMR system, it is necessary to provide a novel structure of an NMR measurement system in order to solve the problem of inaccurate fat detection caused by the non-ideal excitation region.

SUMMARY

In order to solve the problem of inaccurate fat detection caused by a non-ideal excitation region of a single-sided magnet NMR system, an objective of the present disclosure is to provide a novel NMR measurement system for non-invasive quantitative detection of organs.

First, the present disclosure provides an NMR measurement system for non-invasive quantitative detection of organs, including an RF subsystem and a magnet. The magnet is configured to generate a static magnetic field in a detection region.

The RF subsystem includes an NMR spectrometer, an RF power amplifier, a pre-amplifier, a transmit/receive (T/R) switch, and an RF coil group. The RF coil group includes a main RF coil and secondary RF coils. The secondary RF coils are arranged in a peripheral region of the main RF coil and is parallel to the main RF coil.

A pulse sequence signal output port and a pre-saturation pulse signal output port of the NMR spectrometer are electrically connected to a signal input port of the RF power amplifier separately. A pulse sequence signal output port of the RF power amplifier is electrically connected to a first switching port of the T/R switch. A pre-saturation pulse signal output port of the RF power amplifier is electrically connected to the secondary RF coils. An echo signal input port of the pre-amplifier is electrically connected to a second switching port of the T/R switch. An echo signal output port of the pre-amplifier is electrically connected to an echo signal input port of the NMR spectrometer. A gating port of the T/R switch is communicatively connected to a control signal output port of the NMR spectrometer. A common switch port of the T/R switch is electrically connected to the main RF coil.

The main RF coil is configured as a signal transceiver component of the RF subsystem to transmit a pulse sequence signal from the NMR spectrometer, which generates a pulse vector magnetic field intersecting with the static magnetic field in the detection region; and to receive an echo signal from the detection region.

The secondary RF coils are configured as signal transmitting components of the RF subsystem to transmit a pre-saturation pulse signal from the NMR spectrometer before or during transmission of the pulse sequence signal, generating an RF field covering a non-region-of-interest (ROI) in the detection region, such that some or all of magnetization vectors in the non-ROI are parallel to the static magnetic field.

Based on the above content, a novel NMR measurement system that can achieve regional selective excitation can be provided, that is, parallel secondary RF coils are arranged in the peripheral region of the main RF coil of the RF subsystem, and before or during transmission of the pulse sequence signal, the pre-saturation pulse signal is transmitted through the secondary RF coils to generate the RF field covering the non-ROI in the detection region, such that some or all of the magnetization vectors in the non-ROI are parallel to the static magnetic field generated by the magnet. Therefore, unwanted signals generated in the non-ROI interfering with an echo signal generated in an ROI can be weakened or eliminated during measurement. Hence regional selective excitation is achieved, and the problem of inaccurate fat detection caused by a non-ideal excitation region of existing single-sided magnet NMR systems is solved. In addition, since it is based on low-field NMR and a traditional magnetic resonance system is simplified for specific needs, the system is more lightweight and convenient, and more economic benefits can also be produced. Imaging is not needed, the measurement time is short, and the accuracy is high. Based on the NMR technique, the measurement process is highly streamlined, operator-independent, has good repeatability, and is not easily affected by motion.

In a possible design, the RF subsystem may further include an RF field shielding plate, and the RF field shielding plate may be arranged in the peripheral region of the main RF coil and is parallel to the main RF coil.

The RF field shielding plate may be configured to shield the main RF coil from generating the pulse vector magnetic field on the non-ROI when the main RF coil transmits the pulse sequence signal.

In a possible design, the RF field shielding plate may have a flat plate structure, a folding fan structure, or a structure of any combinations thereof, and the flat plate structure and the folding fan structure may be each made of a metal material.

In a possible design, the NMR measurement system may further include a bed body, a shielding chamber, and a movable probe. The shielding chamber may include an internal metal shielding layer.

The shielding chamber may cover a human-bearing bed surface of the bed body, and may have an opening and closing structure to allow a subject to enter a space enclosed by the human-bearing bed surface and the shielding chamber.

The movable probe may be arranged in the space enclosed by the human-bearing bed surface and the shielding chamber, and may be configured to move in the right-left (RL) direction, superior-inferior (SI) direction and/or anterior-posterior (AP) direction of the subject through a mechanical driving mechanism, enabling accurate positioning targeting the to-be-detected organs noninvasively.

In a possible design, the bed body may be grounded, and the metal shielding layer in the shielding chamber may be electrically connected to the bed body through a detachable connecting structure located at an opening and closing edge when a chamber body is closed, such that the metal shielding layer is grounded through the bed body.

In a possible design, the shielding chamber may include a trunk shielding chamber and/or a leg shielding chamber. The trunk shielding chamber and the leg shielding chamber may be configured to be combined to form a closed structure for covering the body below the neck.

The trunk shielding chamber may include a flexible neckline and a shielding sleeve portion. The flexible neckline may be configured to allow a subject's head to reach out of the chamber. The shielding sleeve portion may be configured to allow an arm portion of the subject to reach out of the chamber, and hold a grounding handle.

In a possible design, the grounding handle may be made of a conductive material, and may be grounded through a surge protection circuit.

In a possible design, the NMR measurement system may further include a phase synthesizer and at least one noise measurement coil. At least one noise measurement coil may be arranged in the space enclosed by the human-bearing bed surface and the shielding chamber and far away from the movable probe.

Each noise measurement coil in the at least one noise measurement coil may be electrically connected to a noise signal input port of the pre-amplifier. A noise signal output port of the pre-amplifier may be electrically connected to a signal input port of the phase synthesizer. A signal output port of the phase synthesizer may be electrically connected to a noise signal input port of the NMR spectrometer.

The NMR spectrometer may be further configured to determine a signal correlation between a first noise signal and a second noise signal before acquisition of the echo signal, where the first noise signal may be received from the main RF coil and the second noise signal may be received from the at least one noise measurement coil when the RF power amplifier is turned off.

The NMR spectrometer may be further configured to determine a noise signal in the echo signal from the main RF coil according to the signal correlation between the first noise signal and the second noise signal and a third noise signal from the at least one noise measurement coil during acquisition of the echo signal, and then subtract the determined noise signal from the echo signal to obtain a new echo signal with noise reduction.

In a possible design, the shielding chamber may be hinged with an edge of the human-bearing bed surface of the bed body through a hinge structure.

In a possible design, the magnet may have a single-sided magnet structure, and the single-sided magnet structure may have an ergonomic arc surface fitting with a body surface adjacent to a target organ for detection.

The present disclosure has the following beneficial effects:

(1) The invention of the present disclosure provides a novel NMR measurement system that can achieve regional selective excitation, that is, parallel secondary RF coils are arranged in the peripheral region of the main RF coil of the RF subsystem, and before or during transmission of the pulse sequence signal, the pre-saturation pulse signal is transmitted through the secondary RF coils to generate the RF field covering the non-ROI in the detection region, such that some or all of the magnetization vectors in the non-ROI are parallel to the static magnetic field generated by the magnet. Therefore, unwanted signals generated in the non-ROI interfering with an echo signal generated in an ROI can be weakened or eliminated during measurement. Hence regional selective excitation is achieved, and the problem of inaccurate fat detection caused by a non-ideal excitation region of existing single-sided magnet NMR systems is solved.

(2) Since it is based on low-field NMR and the traditional magnetic resonance system is simplified for specific needs, the system is more lightweight and convenient, and more economic benefits can also be produced. Imaging is not needed, the measurement time is short, and the accuracy is high. Based on the NMR technique, the measurement process is highly streamlined, operator-independent, has good repeatability, and is not easily affected by motion.

(3) By arranging parallel RF field shielding plates in the peripheral region of the main RF coil of the RF subsystem, part of the RF field of the main RF coil can be shielded, such that unwanted signals such as subcutaneous fat are not excited, and regional selective excitation is further improved.

(4) Through active noise control design, the sensitivity of NMR applications to noise can be reduced, and the accuracy of the measurement results can be further ensured.

BRIEF DESCRIPTION OF THE DRAWINGS

To describe the technical solutions in the embodiments of the present invention or in the prior art more clearly, the following briefly describes the accompanying drawings required for describing the embodiments or the prior art. Apparently, the accompanying drawings in the following description show merely some embodiments of the present invention, and a person of ordinary skill in the art may still derive other drawings from these accompanying drawings without creative efforts.

FIG. 10 is a schematic diagram of magnetic field decomposition of the main RF coil and an RF field shielding plate provided by the present disclosure;

FIG. 11A is a single-layer flat plate structure, FIG. 11B is a single-layer folding fan structure, FIG. 11C is a combined structure of a lower flat plate and an upper folding fan, FIG. 11D is a double-layer flat plate structure, and FIG. 11E is a double-layer folding fan structure;

DETAILED DESCRIPTION OF THE EMBODIMENTS

Figure 1:
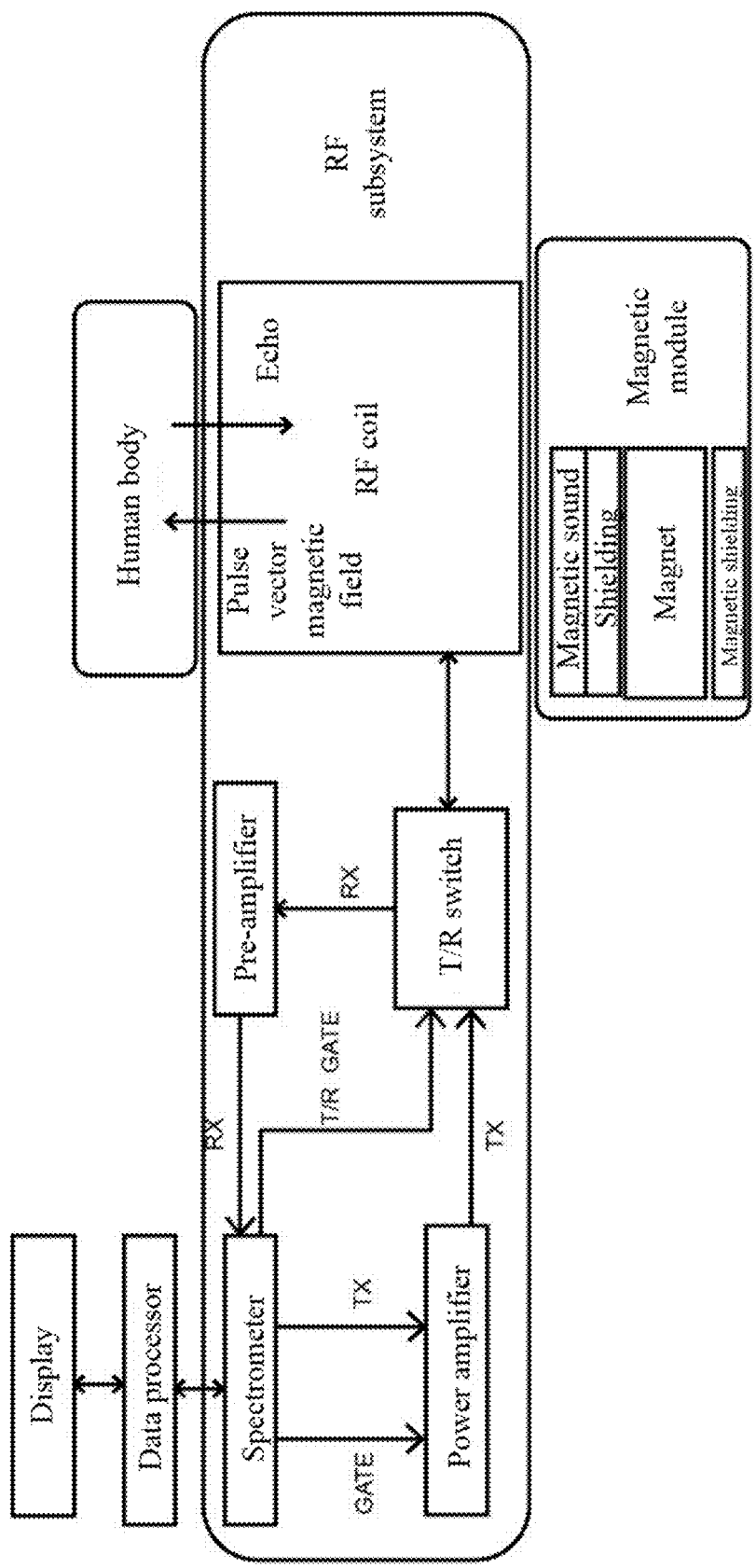
FIG. 1 is a schematic structural diagram of a system for non-invasive quantitative detection of organ fat based on LF-NMR in the prior art.
Figure 2:
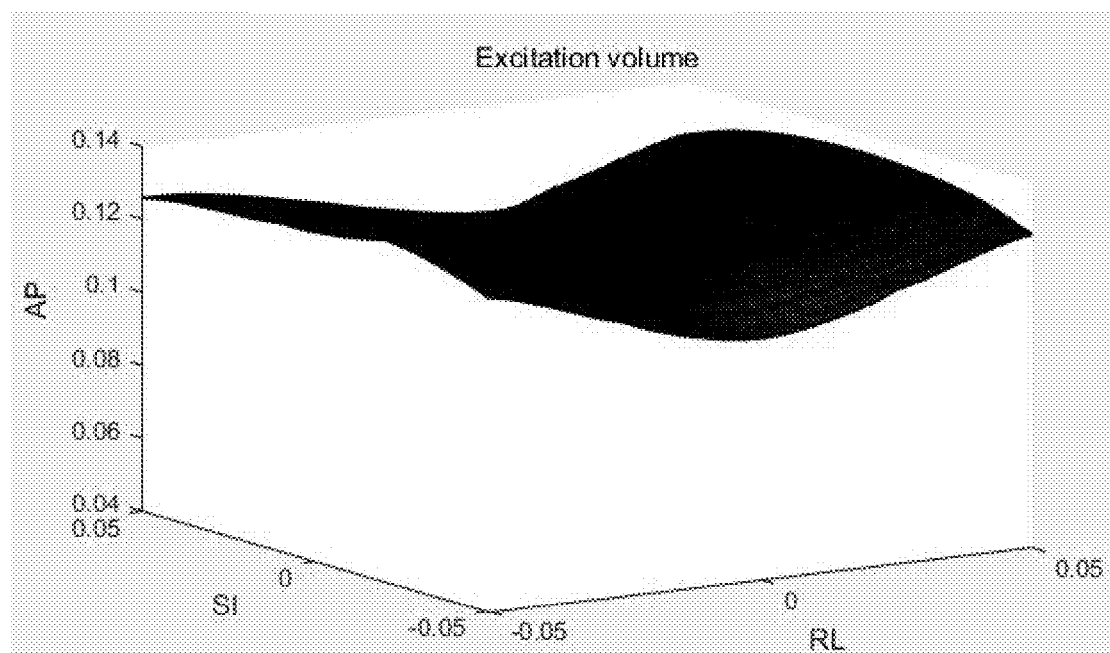
FIG. 2 is an exemplary simulation diagram of an excitation region of a single-sided magnet NMR system in the prior art.

The present disclosure will be further described below with reference to the accompanying drawings and specific embodiments. It should be noted here that the description of these embodiments is used to help understand the present disclosure, but does not constitute a limitation to the present disclosure. The specific structural and functional details disclosed herein are only used to describe illustrative embodiments of the present disclosure. However, the present disclosure may be embodied in many alternative forms, and it should not be understood that the present disclosure is limited to the examples set forth herein.

It should be understood that although the terms such as "first" and "second" may be used herein to describe various units, these units should not be limited by these terms. These terms are only used to distinguish one unit from another. For example, a first unit may be referred to as a second unit, and a second unit may be referred to as a first unit similarly, without departing from the scope of the illustrative embodiments of the present disclosure.

It should be understood that the term "and/or" that may be used herein only refers to an association relationship for describing associated objects and represents that there may be three relationships. For example, A and/or B may represent the following three cases: there is A alone; there is B alone; and there are both A and B. The term "/and" that may be used herein refers to another relationship between associated objects and represents that there may be two relationships. For example, A/and B may represent the following two cases: there is A alone, and there are both A and B. In addition, the character "/" that may be used herein generally indicates an "or" relationship between the associated objects before and after the character.

It should be understood that in the description where a unit is "connected to", "connected to", or "coupled with" another unit, the unit can be connected or coupled to the other unit directly or through an intermediate unit. In contrast, in the description where a unit is "directly connected" or "directly coupled" to another unit, there is no intermediate unit. In addition, other words used to describe relationships among units should be interpreted in a similar way (for example, "between" vs "directly between", "adjacent" vs "directly adjacent", etc.).

It should be understood that the terms used herein are only used to describe specific embodiments, and are not intended to limit illustrative embodiments of the present disclosure. As used herein, the singular forms "a", "an", and "the" are intended to include plural forms, unless the context clearly indicates the opposite. It should also be understood that the terms "include", "may include", "comprises", and/or "may comprise", when used herein, specify the existence of the stated features, integers, steps, operations, units, and/or components, which do not exclude the existence or addition of one or more other features, quantities, steps, operations, units, and components, and/or combinations thereof.

It should also be noted that in some alternative designs, the functions/actions may appear in an order different from that shown in the figures. For example, some involved functions/actions may actually be executed substantially concurrently, or sometimes two figures shown in succession may be executed in a reverse order.

It should be understood that specific details are provided in the following description to facilitate a complete understanding of the illustrative embodiments. However, those of ordinary skill in the art should understand that the illustrative embodiments can be implemented without these specific details. For example, the system can be shown in a block diagram to avoid the problem that an example is illustrated unclearly due to unnecessary details. In other examples, well-known procedures, structures, and technologies may not be shown in unnecessary details to avoid making the illustrative embodiments unclear.

As shown in FIG. 3 to FIG. 9, an NMR measurement system for non-invasive quantitative detection of organs provided by a first aspect of the present embodiment includes an RF subsystem and a magnet 2. The magnet 2 is configured to generate a static magnetic field in a detection region. The RF subsystem includes an NMR spectrometer, an RF power amplifier, a pre-amplifier, a T/R switch, and an RF coil group. The RF coil group includes a main RF coil 151 and secondary RF coils 152. The secondary RF coils 152 are arranged in a peripheral region of the main RF coil 151 and is parallel to the main RF coil 151. A pulse sequence signal output port and a pre-saturation pulse signal output port of the NMR spectrometer are electrically connected to a signal input port of the RF power amplifier separately. A pulse sequence signal output port of the RF power amplifier is electrically connected to a first switching port of the T/R switch. A pre-saturation pulse signal output port of the RF power amplifier is electrically connected to the secondary RF coils 152. An echo signal input port of the pre-amplifier is electrically connected to a second switching port of the T/R switch. An echo signal output port of the pre-amplifier is electrically connected to an echo signal input port of the NMR spectrometer. A gating port of the T/R switch is communicatively connected to a control signal output port of the NMR spectrometer. A common switch port of the T/R switch is electrically connected to the main RF coil 151. The main RF coil 151 is configured as a signal transceiver component of the RF subsystem to transmit a pulse sequence signal from the NMR spectrometer to generate a pulse vector magnetic field intersecting with the static magnetic field in the detection region, and receive an echo signal from the detection region. The secondary RF coils 152 are configured as signal transmitting components of the RF subsystem to transmit a pre-saturation pulse signal from the NMR spectrometer before or during transmission of the pulse sequence signal, generating an RF field covering a non-ROI in the detection region, such that some or all of magnetization vectors in the non-ROI are parallel to the static magnetic field.

Figure 3:
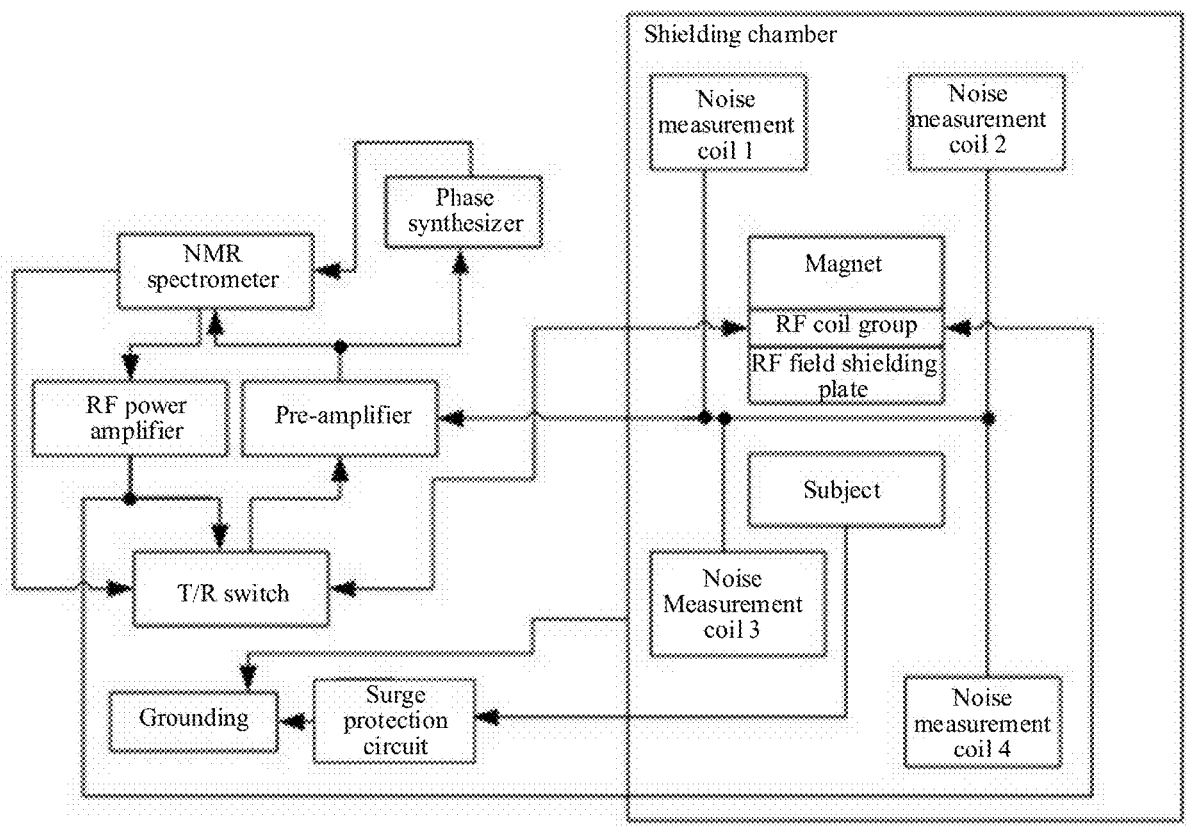
FIG. 3 is a schematic structural diagram of an NMR measurement system provided by the present disclosure.
Figure 4:
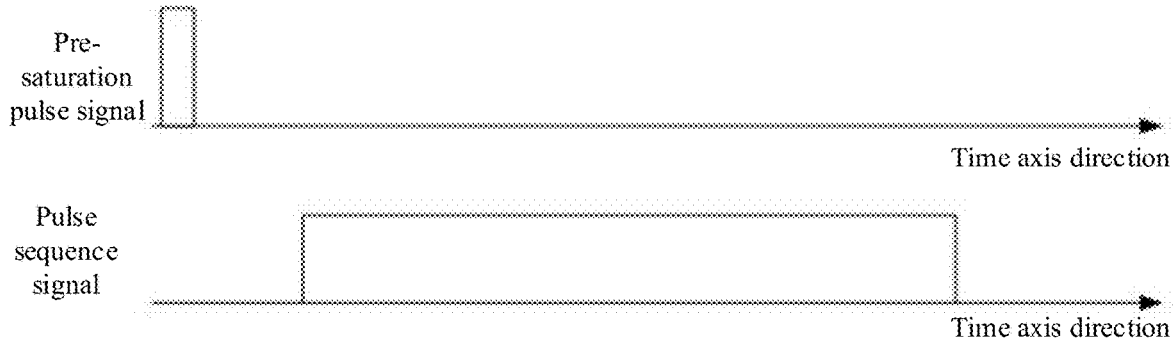
FIG. 4 is a first timing diagram of a pulse sequence signal and a pre-saturation pulse signal provided by the present disclosure.
Figure 5:
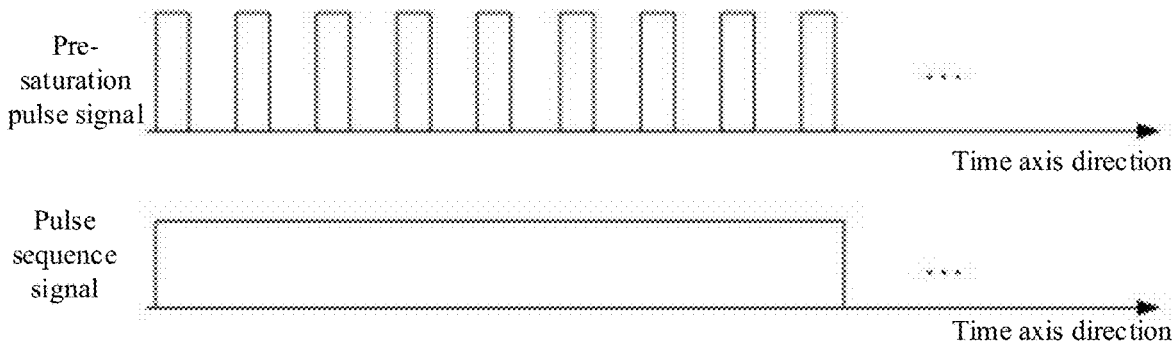
FIG. 5 is a second timing diagram of the pulse sequence signal and the pre-saturation pulse signal provided by the present disclosure.

As shown in FIG. 3 to FIG. 9, in a specific structure of the NMR measurement system, the NMR spectrometer is configured to generate the pulse sequence signal (which is an existing scanning pulse sequence signal configured to excite hydrogen atoms in a target for detection and generate a detectable signal, also known as a magnetic resonance signal or an echo signal) and the pre-saturation pulse signal as shown in FIG. 4 or FIG. 5 in an existing conventional way, to drive one or more of the main RF coils 151 and one or more of the secondary RF coils 152, and perform measurement processing on the received echo signal to achieve non-invasive quantitative detection of the organs, which can be realized by using existing instruments and equipment. The RF power amplifier is configured to amplify the pulse sequence signal and the pre-saturation pulse signal to be transmitted. The pre-amplifier is configured to amplify the received echo signal. The T/R switch is configured to switch and control a gate control signal, such that the main RF coil 151 can both transmit the pulse sequence signal and asynchronously receive the echo signal, and it may be, but is not limited to, a single-pole double-throw (SPDT) switch.

Figure 6:
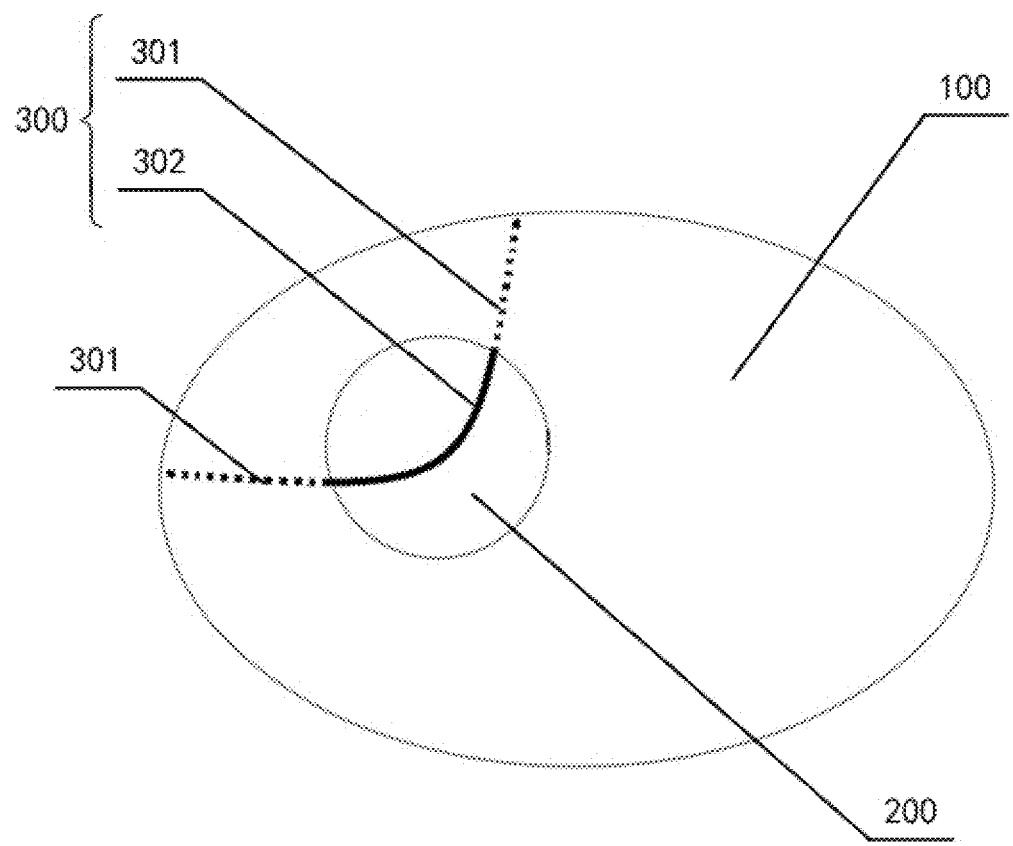
FIG. 6 is a schematic cross-sectional view of a human body provided by the present disclosure.
Figure 7:
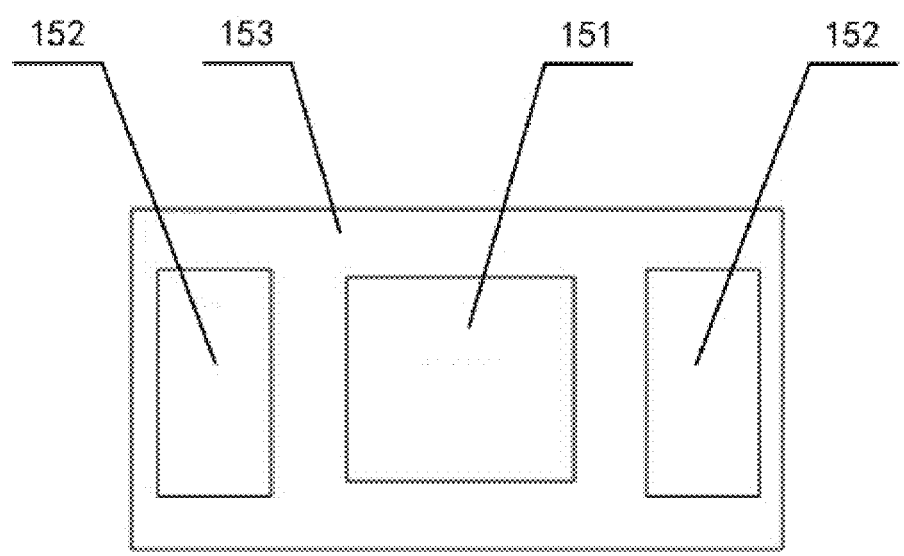
FIG. 7 is a schematic diagram of a first arrangement of a main RF coil and secondary RF coils provided by the present disclosure.
Figure 8:
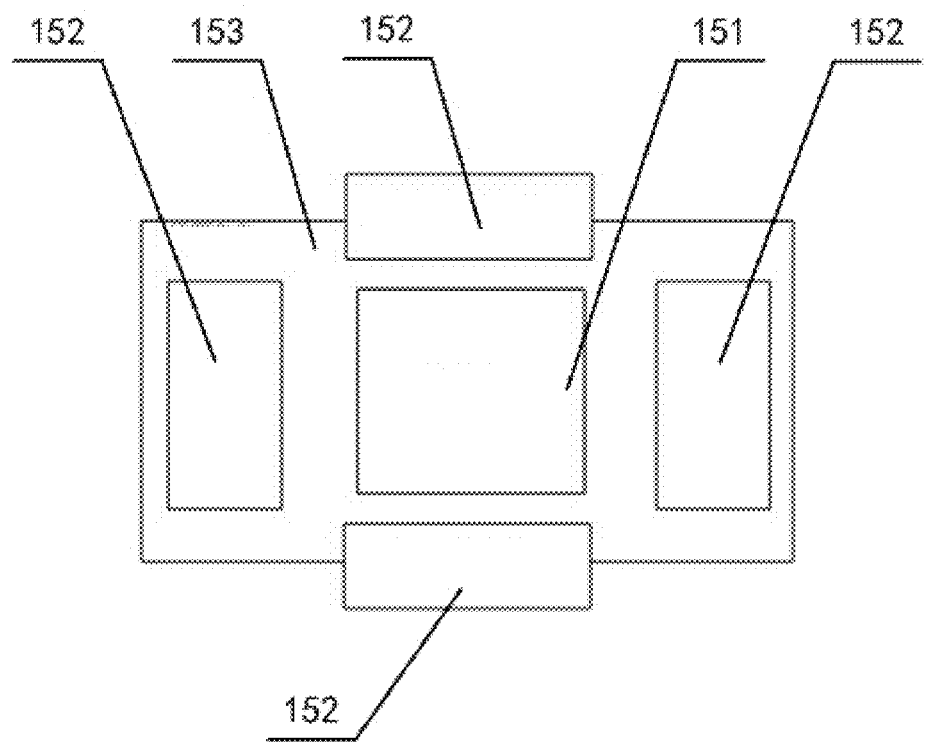
FIG. 8 is a schematic diagram of a second arrangement of the main RF coil and the secondary RF coils provided by the present disclosure.

When the pulse vector magnetic field generated by the main RF coil 151 in the detection region is orthogonal to the static magnetic field, the efficiency of excitation is the highest, and the frequency of the pulse vector magnetic field is adjustable to match the Larmor frequency (which is the $^1$H gyromagnetic ratio multiplied by the field strength of the static magnetic field) at different locations within an ROI. The RF field generated by the secondary RF coils 152 is also adjustable. Within its RF field coverage, the pre-saturation pulse signal (which preferably can generate a pulse signal with a flip angle of 90 degrees) can be continuously applied before (as shown in FIG. 4) or during (as shown in FIG. 5) transmission of the pulse sequence signal, such that some or all of the magnetization vectors in the non-ROI are parallel to the static magnetic field. Therefore, unwanted signals generated in the non-ROI (such as the subcutaneous fat) interfering with the echo signal generated in the ROI (such as the liver) can be weakened or eliminated during measurement. Hence regional selective excitation is achieved. As shown in FIG. 6, in the schematic cross-sectional view of the human body, an arc 300 is the excitation region (that is, the detection region) of the main RF coil 151. In the case of no saturation, all signals in this region are received, that is, a solid line segment 302 in the arc 300 is the ROI (that is, the target organ 200), and a dotted line segment 301 in the arc 300 is the non-ROI (that is, the region to be saturated). The signal from the non-ROI will cause errors to the measurement results. If the non-ROI is pre-saturated by the secondary RF coils 152, the signal from the non-ROI can be reduced or eliminated. In addition, as shown in FIG. 7, the number of the secondary RF coils 152 may be two, and they are symmetrically arranged in the peripheral region of the main RF coil 151 and horizontally arranged on a coil base 153 together with the main RF coil 151. As shown in FIG. 8, the number of the secondary RF coils 152 may be four, and they are symmetrically arranged in the peripheral region of the main RF coil 151 up and down and left and right and horizontally arranged on the coil base 153 together with the main RF coil 151.

Figure 9:
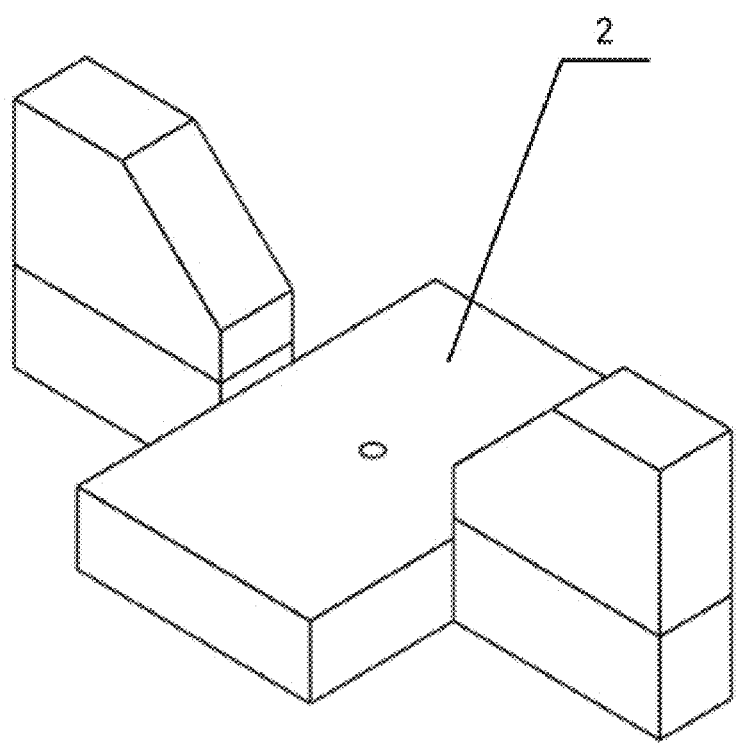
FIG. 9 is a schematic three-dimensional structural diagram of a single-sided magnet structure provided by the present disclosure.
Figure 11A:
FIGS. 11A-11E are schematic diagrams showing a specific structure of the RF field shielding plate provided by the present disclosure, where
Figure 11B:
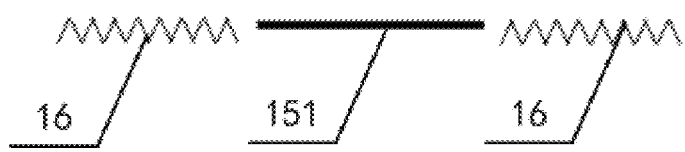
Figure 11C:
Figure 11D:
Figure 11E:
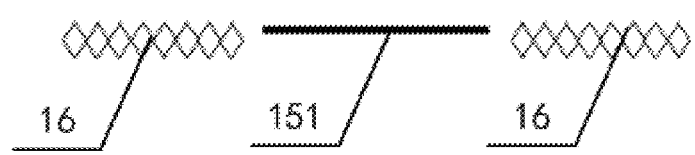

The magnet 2 is a portable magnet, and the portable magnet has at least a single-sided magnet structure. The single-sided magnet structure has an ergonomic arc surface fitting with a body surface adjacent to a target organ for detection, as shown in FIG. 9. The static magnetic field generated by the magnet 2 is configured to polarize the hydrogen atoms in the ROI of the target for detection. Using the single-sided magnet structure as shown in FIG. 9, the excitation region of the static magnetic field can reach a typical depth of 12 cm from the surface of the magnet and 9 cm under the skin, which can also achieve good selectivity for patients with a thick subcutaneous fat layer. The excitation region of the static magnetic field is highly selective in the ROI along the depth direction, which can avoid signals from organs other than the liver. In addition, the magnet 2 may also be a permanent magnet, an electromagnet, or a combination thereof.

Thus, through detailed description of the aforementioned NMR measurement system, a novel NMR measurement system that can achieve regional selective excitation is provided, that is, parallel secondary RF coils are arranged in the peripheral region of the main RF coil of the RF subsystem, and before or during transmission of the pulse sequence signal, the pre-saturation pulse signal is transmitted through the secondary RF coils to generate the RF field covering the non-ROI in the detection region, such that some or all of the magnetization vectors in the non-ROI are parallel to the static magnetic field generated by the magnet. Therefore, unwanted signals generated in the non-ROI interfering with an echo signal generated in an ROI can be weakened or eliminated during measurement. Hence regional selective excitation is achieved, and the problem of inaccurate fat detection caused by a non-ideal excitation region of existing single-sided magnet NMR systems is solved. In addition, since it is based on low-field NMR and the traditional magnetic resonance system is simplified for specific needs, the system is more lightweight and convenient, and more economic benefits can also be produced. Imaging is not needed, the measurement time is short, and the accuracy is high. Based on the NMR technique, the measurement process is highly streamlined, operator-independent, has good repeatability, and is not easily affected by motion.

Figure 12:
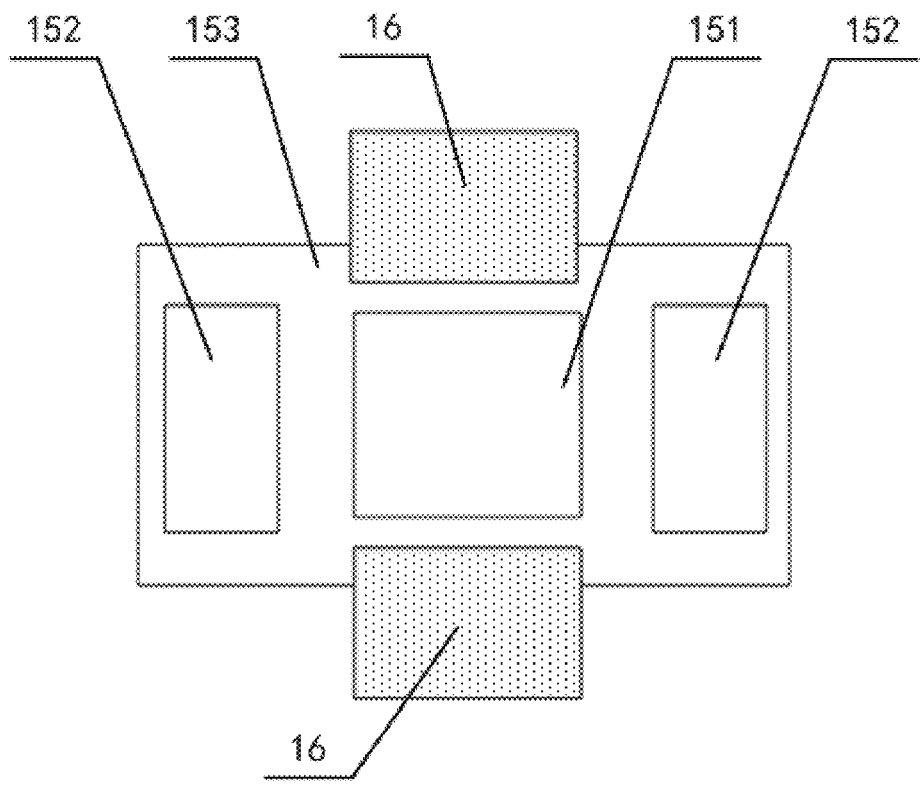
FIG. 12 is a schematic diagram of arrangement of the main RF coil, secondary RF coils, and the RF field shielding plate provided by the present disclosure.

In a possible design, the RF subsystem further includes an RF field shielding plate 16, and the RF field shielding plate 16 is arranged in the peripheral region of the main RF coil 151 and is parallel to the main RF coil 151. The RF field shielding plate 16 is configured to shield the main RF coil 151 from generating the pulse vector magnetic field on the non-ROI when the main RF coil 151 transmits the pulse sequence signal. As shown in FIG. 10, the RF field shielding plate 16 may be made of metal, and its working principle is as follows: when an RF current passes through the main RF coil 151, the RF current generates a time-varying magnetic field (which can be called a main magnetic field), and induces a current in the RF field shielding plate 16 that flows in the same direction as the current of the RF coil, and flows in the form of eddy current in the RF field shielding plate 16. A magnetic field generated by this induced current and the magnetic field generated by the RF current are superimposed with each other. Since the RF field shielding plate 16 is a complete metal body, the current induced on a shielding body flows in a multi-cycle path, and changes with the main magnetic field. Most of the magnetic fields generated by the current in these paths are superimposed in the y direction, while the superposition effect in the x direction is weak. In the region close to the RF field shielding plate 16, the main magnetic field enters the region on the RF field shielding plate 16 in a direction almost perpendicular to the RF field shielding plate 16. Therefore, in the region close to the RF field shielding plate 16, the component of the main magnetic field is mainly the y component. Thus, in the region of the RF field shielding plate 16, the magnetic field generated by the induced current and the main magnetic field are superimposed with each other in the y direction, such that the main magnetic field is greatly weakened in a certain region on the RF field shielding plate 16. However, in the x direction of the region close to the RF field shielding plate 16, the superposition of some regions and the main magnetic field is enhanced, and some regions are weakened. Since the main magnetic field has less component in the x direction of the region close to the RF field shielding plate 16, and the component of the induced current in the x direction is also relatively weak, such that the component in the y direction in this region is greatly weakened, resulting in a substantial reduction of the main magnetic field in a certain region close to the RF field shielding plate 16. Therefore, by adjusting a distance between the RF field shielding plate 16 and the main RF coil 151, part of the RF field of the main RF coil 151 can be shielded, such that unwanted signals such as subcutaneous fat are not excited, and regional selective excitation is achieved. As shown in FIGS. 11A-11E, the RF field shielding plate 16 may have, but not limited to, a flat plate structure, a folding fan structure, or a structure of any combinations thereof, and the flat plate structure and the folding fan structure are each made of a metal material. Using the folding fan structure, the paths of induced current circulation increase, which further increase the induced magnetic field in the region close to the RF field shielding plate 16, and improve the ability to weaken the main magnetic field in the region close to the RF field shielding plate 16. In addition, arrangement positions of the RF field shielding plate 16 and the secondary RF coils 152 in the peripheral region of the main RF coil 151 may be, for example, shown in FIG. 12.

Figure 13:
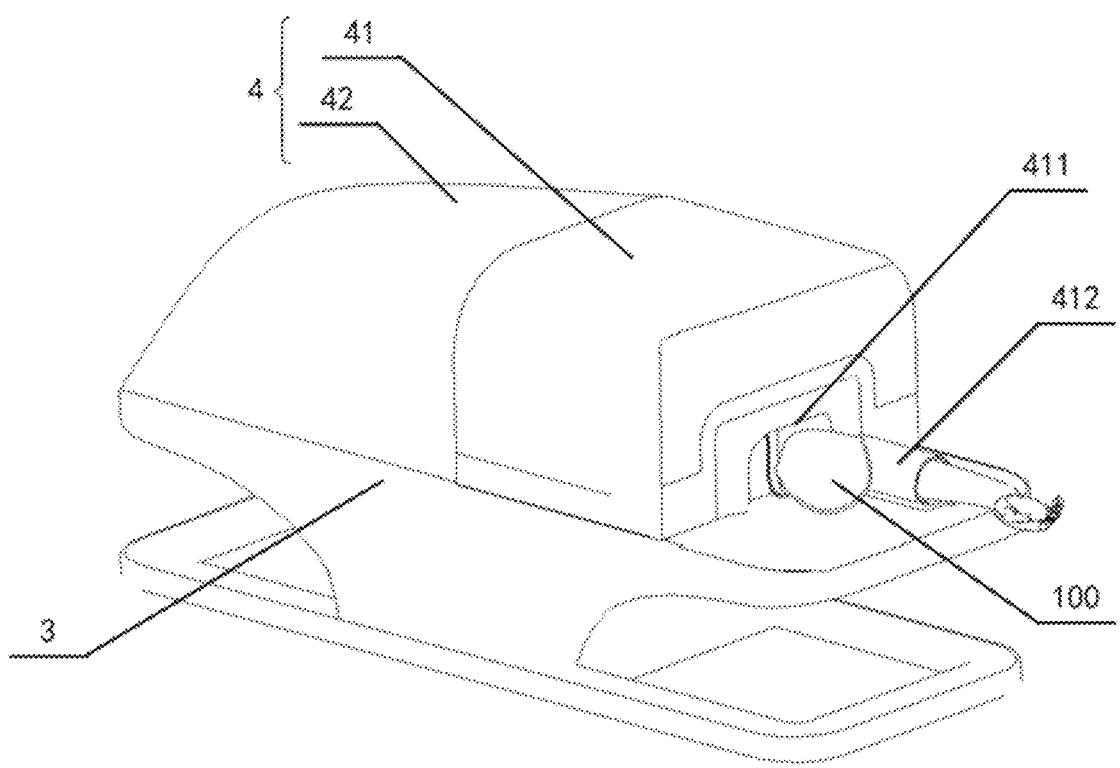
FIG. 13 is a schematic diagram of a first use structure of a bed body and a shielding chamber provided by the present disclosure.
Figure 14:
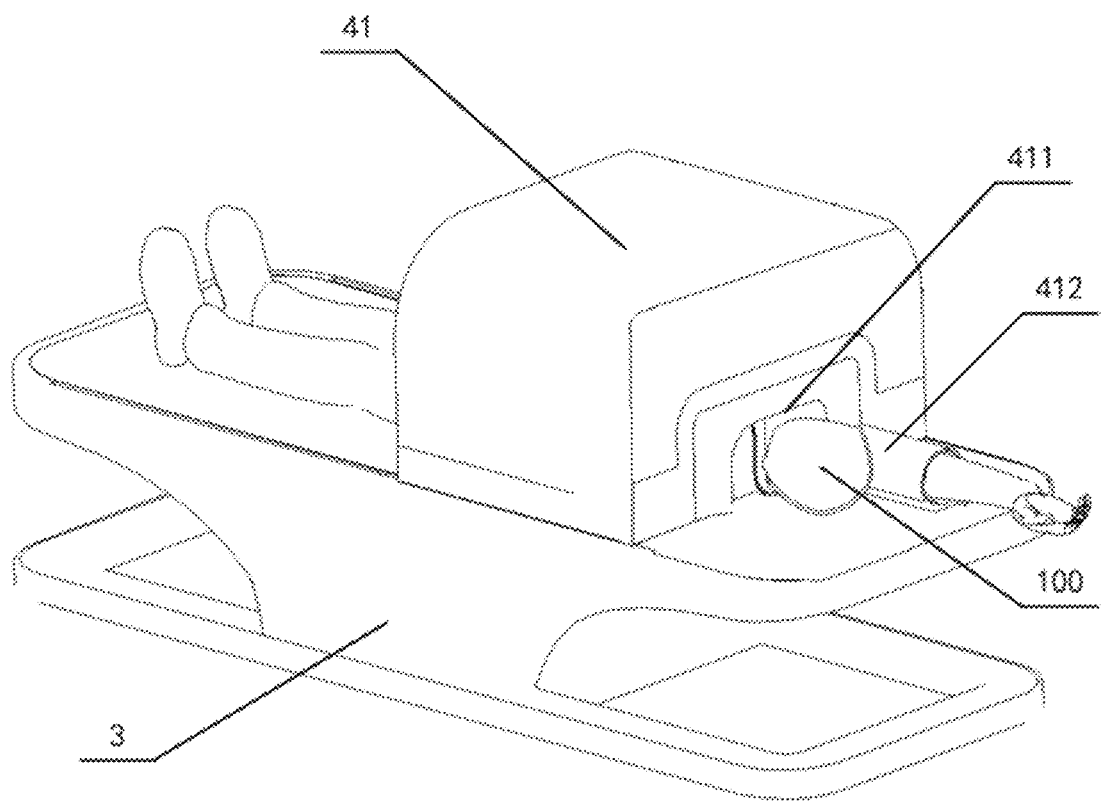
FIG. 14 is a schematic diagram of a second use structure of the bed body and the shielding chamber provided by the present disclosure.
Figure 15:
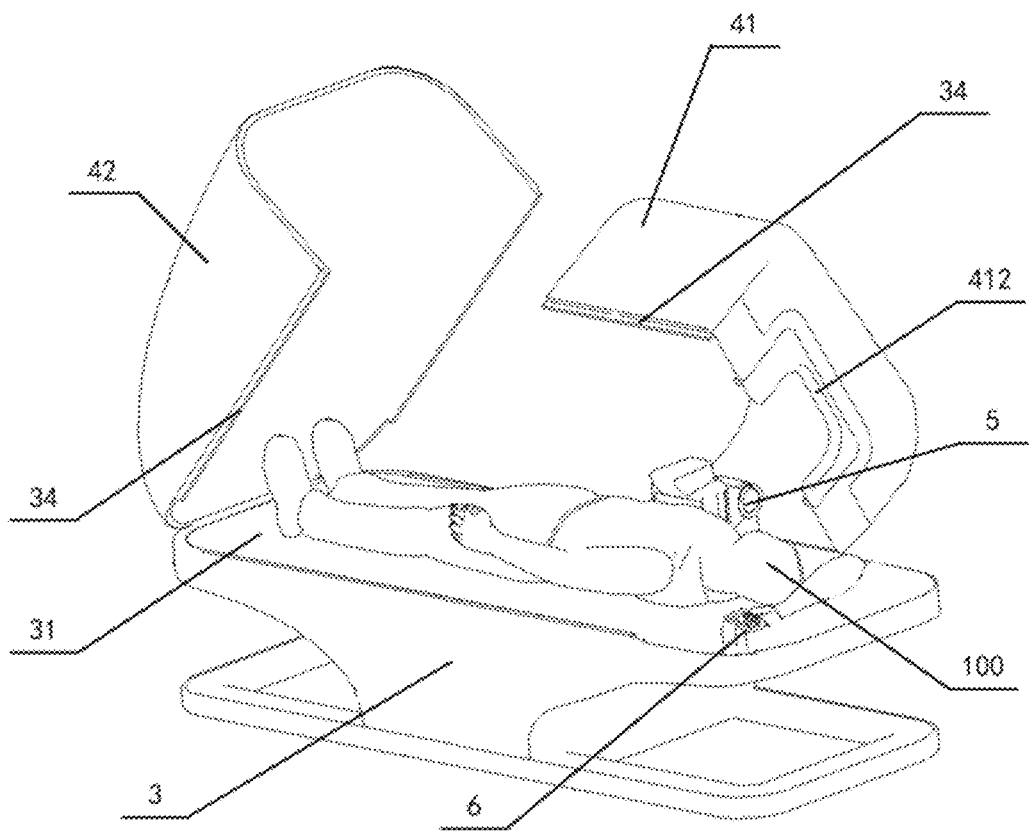
FIG. 15 is a schematic diagram of an opening structure of the bed body and the shielding chamber provided by the present disclosure.
Figure 16:
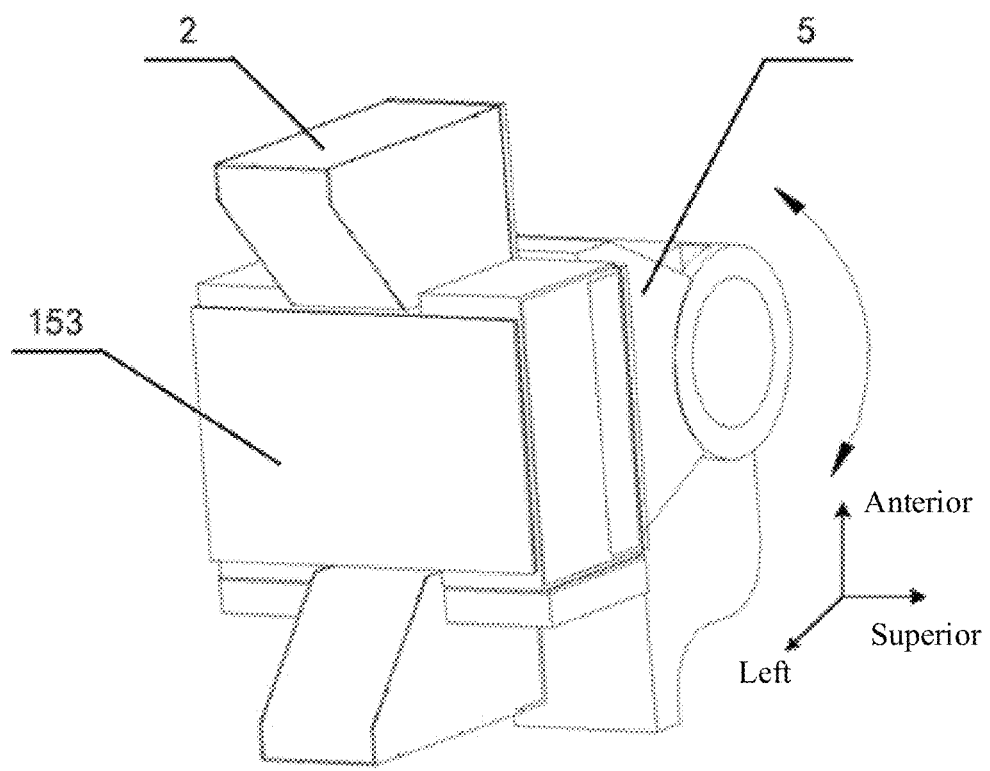
FIG. 16 is a schematic three-dimensional structural diagram of a movable probe provided by the present disclosure.

In a possible design, the NMR measurement system further includes a bed body 3, a shielding chamber 4, and a movable probe 5. The shielding chamber 4 includes an internal metal shielding layer. The shielding chamber 4 covers a human-bearing bed surface 31 of the bed body 3, and has an opening and closing structure to allow a subject to enter a space enclosed by the human-bearing bed surface 31 and the shielding chamber 4. The movable probe 5 is arranged in the space enclosed by the human-bearing bed surface 31 and the shielding chamber 4, and is configured to move in the RL direction, SI direction and/or AP direction of the subject through a mechanical driving mechanism, which enables accurate positioning targeting the to-be-detected organs noninvasively. As shown in FIG. 13 to FIG. 15, the bed body 3 is configured to bear the subject 100. In addition to shielding external interference signals, the shielding chamber 4 can also effectively protect the movable probe 5. It can be made of a hard material and sandwiched with the metal shielding layer, such as a metal mesh, a metal film, or a metal sheet. The shielding chamber 4 is hinged with an edge of the human-bearing bed surface of the bed body 3 through a hinge structure, to be opened and closed to allow the subject 100 to enter. The movable probe 5 is configured to load the RF coil group, the RF field shielding plate 16, and the magnet 2, to move in the RL direction, the SI direction and/or the AP direction of the subject through the mechanical driving mechanism, which enables accurate positioning targeting the to-be-detected organs noninvasively, as shown in FIG. 16. Specifically, the bed body 3 is grounded, and the metal shielding layer in the shielding chamber 4 is electrically connected to the bed body 3 through a detachable connecting structure 34 located at an opening and closing edge when a chamber body is closed, such that the metal shielding layer is grounded through the bed body 3. The detachable connecting structure 34 may be, but is not limited to, a structure in which a reed or a plug is matched with a reserved slot, to achieve overall electrical conduction between the shielding chamber 4 and the entire patient bed, and ensure the shielding effect of the shielding chamber 4.

In a possible design, the shielding chamber 4 includes a trunk shielding chamber 41/and a leg shielding chamber 42, and the trunk shielding chamber 41 and the leg shielding chamber 42 are configured to be combined to form a closed structure for covering the body below the neck. The trunk shielding chamber 41 includes a flexible neckline 411 and a shielding sleeve portion 412. The flexible neckline 411 is configured to allow the head of the subject to reach out of the chamber. The shielding sleeve portion 412 is configured to allow an arm portion of the subject to reach out of the chamber and hold a grounding handle 6. As shown in FIG. 13, the trunk shielding chamber 41 and the leg shielding chamber 42 are configured to be combined to form the closed structure for covering the body below the neck, while as shown in FIG. 14, there may be only a semi-closed structure (that is, a semi-open type shielding chamber structure) formed by the trunk shielding chamber 41. The flexible neckline 411 is configured for matching with the neck of the subject 100. The shielding sleeve portion 412 is configured for matching with the arm portion of the subject 100, and can help the subject 100 to be fixed for a testing posture. The grounding handle 16 is configured to eliminate noise that may be introduced by the human body, and specifically, the grounding handle 6 is made of a conductive material, and is grounded through a surge protection circuit. In this way, the subject 100 can hold the grounding handle 6 during measurement to ground the noise signal conducted through the human body to eliminate it. In detail, the surge protection circuit may be designed as a resistor-capacitor (RC) parallel filter circuit, to form a high-pass filter with a cutoff frequency of about 60 Hz, that is, the filter circuit has a high impedance at 60 Hz and a very low impedance at a target frequency. The human body releases the noise induced by the human body by touching the metal rod. If the grounding metal rod is directly touched without the protection circuit, and this ground is connected to the ground of the outer shielding and components such as the power amplifier, it may transmit instantaneous high voltage or large current (mainly working frequency) through the shielding layer, which may cause danger. Since the noise from the human body is usually high-frequency noise, the capacitor has a very low impedance at the target frequency. Therefore, the noise can be released to the ground, and the high-pass filter has a high impedance at the working frequency, which can prevent the passage of large currents, thereby protecting the human body.

In a possible design, the NMR measurement system further includes a phase synthesizer and at least one noise measurement coil. The at least one noise measurement coil is arranged in the space enclosed by the human-bearing bed surface and the shielding chamber and far away from the movable probe. Each noise measurement coil in the at least one noise measurement coil is electrically connected to a noise signal input port of the pre-amplifier. A noise signal output port of the pre-amplifier is electrically connected to a signal input port of the phase synthesizer. A signal output port of the phase synthesizer is electrically connected to a noise signal input port of the NMR spectrometer. The NMR spectrometer is further configured to determine a signal correlation between a first noise signal and a second noise signal before acquisition of the echo signal, where the first noise signal is received from the main RF coil 151 and the second noise signal is received from the at least one noise measurement coil when the RF power amplifier is turned off. The NMR spectrometer is further configured to determine a noise signal in the echo signal from the main RF coil 151 according to the signal correlation between the first noise signal and the second noise signal and a third noise signal from the at least one noise measurement coil during acquisition of the echo signal, and then subtract the determined noise signal from the echo signal to obtain a new echo signal with noise reduction. As shown in FIG. 3, the at least one noise measurement coil includes four noise measurement coils. Since the signal received by the coil is related to the distance from a signal source, a large distance indicates a low signal, when the noise measurement coil is placed in the shielding chamber 4, it needs to be arranged far away from the movable probe, to ensure that the magnetic resonance signal/echo signal it receives can be ignored. The noise signal exists in the environment, so it can be considered that the noise measurement coil is only acquiring the noise signal. The phase synthesizer is configured to synthesize noise signals from different noise measurement coils, and then the noise signals are received and processed by the NMR spectrometer. Therefore, when the at least one noise measurement coil has only one noise measurement coil, the phase synthesizer may be omitted. The determination process of the signal correlation can use the existing technology, such as the linear fitting or nonlinear fitting technology. The determination method of the noise signal in the echo signal can still use the existing technology. Although the shielding chamber 4 can block most of the noise from the surrounding environment, due to the incomplete closed structure or open structure of the shielding chamber 4, part of the ambient noise will be introduced through the human body, the shielding chamber, or the patient bed, etc. Therefore, through the aforementioned active noise control design, the sensitivity of NMR applications to noise can be reduced, and the accuracy of the measurement results can be further ensured.

The embodiments described above are merely illustrative, where units described as separate components may or may not be physically separated. Components displayed as units may or may not be physical units, that is, the components may be located in one place, or may be distributed to a plurality of network units. Some or all of the units may be selected according to actual requirements to achieve the objectives of the solutions in the embodiments. Those of ordinary skill in the art can understand and implement the embodiments without creative efforts.

The foregoing embodiments are only used to explain the technical solutions of the present disclosure, and are not intended to limit the same. Although the present disclosure is described in detail with reference to the foregoing embodiments, those of ordinary skill in the art should understand that they can still modify the technical solutions described in the foregoing embodiments, or make equivalent substitutions on some technical features therein. These modifications or substitutions do not make the essence of the corresponding technical solutions deviate from the spirit and scope of the technical solutions of the embodiments of the present disclosure.

Finally, it should be noted that the present disclosure is not limited to the above-mentioned optional implementations, and anyone can derive other products in various forms under the enlightenment of the present disclosure. The above-mentioned specific examples should not be construed as limiting the protection scope of the present disclosure, and the protection scope of the present disclosure should be defined by the claims. Moreover, the description can be used to interpret the claims.

What is claimed is:

1. A nuclear magnetic resonance (NMR) measurement system for non-invasive quantitative detection of organs, comprising a radio frequency (RF) subsystem and a magnet, wherein the magnet is configured to generate a static magnetic field in a detection region;

the RF subsystem comprises an NMR spectrometer, an RF power amplifier, a pre-amplifier, a transmit/receive (T/R) switch, and an RF coil group, wherein the RF coil group comprises a main RF coil and secondary RF coils, and the secondary RF coils are arranged in a peripheral region of the main RF coil and are parallel to the main RF coil;

a pulse sequence signal output port and a pre-saturation pulse signal output port of the NMR spectrometer are electrically connected to a signal input port of the RF power amplifier separately, a pulse sequence signal output port of the RF power amplifier is electrically connected to a first switching port of the T/R switch, a pre-saturation pulse signal output port of the RF power amplifier is electrically connected to the secondary RF coils, an echo signal input port of the pre-amplifier is electrically connected to a second switching port of the T/R switch, an echo signal output port of the pre-amplifier is electrically connected to an echo signal input port of the NMR spectrometer, a gating port of the T/R switch is communicatively connected to a control signal output port of the NMR spectrometer, and a common switch port of the T/R switch is electrically connected to the main RF coil;

the main RF coil is configured as a signal transceiver component of the RF subsystem to transmit a pulse sequence signal from the NMR spectrometer to generate a pulse vector magnetic field intersecting with the static magnetic field in the detection region, and receive an echo signal from the detection region; and the secondary RF coils are configured as signal transmitting components of the RF subsystem to transmit a pre-saturation pulse signal from the NMR spectrometer before or during transmission of the pulse sequence signal, generating an RF field covering a non-region-of-interest (ROI) in the detection region, such that some or all of magnetization vectors in the non-ROI are parallel to the static magnetic field.

2. The NMR measurement system according to claim 1, wherein the RF subsystem further comprises an RF field shielding plate, wherein the RF field shielding plate is arranged in the peripheral region of the main RF coil, and the RF field shielding plate is parallel to the main RF coil; and the RF field shielding plate is configured to shield the main RF coil from generating the pulse vector magnetic field on the non-ROI when the main RF coil transmits the pulse sequence signal.

3. The NMR measurement system according to claim 2, wherein the RF field shielding plate has a flat plate structure, a folding fan structure, or a structure of any combinations of the flat plate structure and the folding fan structure, wherein the flat plate structure and the folding fan structure are each made of a metal material.

4. The NMR measurement system according to claim 1, further comprising a bed body, a shielding chamber, and a movable probe, wherein the shielding chamber includes an internal metal shielding layer;

the shielding chamber covers a human-bearing bed surface of the bed body, and the shielding chamber has an opening and closing structure to allow a subject to enter a space enclosed by the human-bearing bed surface and the shielding chamber; and the movable probe is arranged in the space enclosed by the human-bearing bed surface and the shielding chamber, and the movable probe is configured to move in the right-left (RL) direction, superior-inferior (SI) direction and/or anterior-posterior (AP) direction of the subject through a mechanical driving mechanism, enabling accurate positioning targeting the to-be-detected organs noninvasively.

5. The NMR measurement system according to claim 4, wherein the bed body is grounded, and the internal metal shielding layer in the shielding chamber is electrically connected to the bed body through a detachable connecting structure located at an opening and closing edge when a chamber body of the shielding chamber is closed, such that the internal metal shielding layer is grounded through the bed body.

6. The NMR measurement system according to claim 4, wherein the shielding chamber comprises a trunk shielding chamber and/or a leg shielding chamber, and the trunk shielding chamber and the leg shielding chamber are configured to be combined to form a closed structure for covering a body below the neck; and the trunk shielding chamber comprises a flexible neckline and a shielding sleeve portion, wherein the flexible neckline is configured to allow a subject's head to reach out of the trunk shielding chamber, and the shielding sleeve portion is configured to allow an arm portion of the subject to reach out of the trunk shielding chamber, and hold a grounding handle.

7. The NMR measurement system according to claim 6, wherein the grounding handle is made of a conductive material, and the grounding handle is grounded through a surge protection circuit.

8. The NMR measurement system according to claim 4, further comprising a phase synthesizer and at least one noise measurement coil, wherein the at least one noise measurement coil is arranged in the space enclosed by the human-bearing bed surface and the shielding chamber, and is far away from the movable probe;

each noise measurement coil in the at least one noise measurement coil is electrically connected to a noise signal input port of the pre-amplifier, a noise signal output port of the pre-amplifier is electrically connected to a signal input port of the phase synthesizer, and a signal output port of the phase synthesizer is electrically connected to a noise signal input port of the NMR spectrometer;

the NMR spectrometer is further configured to determine a signal correlation between a first noise signal and a second noise signal before acquisition of the echo signal, wherein the first noise signal is received from the main RF coil and the second noise signal is received from the at least one noise measurement coil when the RF power amplifier is turned off; and the NMR spectrometer is further configured to determine a fourth noise signal in the echo signal from the main RF coil according to the signal correlation between the first noise signal and the second noise signal and a third noise signal from the at least one noise measurement coil during acquisition of the echo signal, and then subtract the fourth noise signal from the echo signal to obtain a new echo signal with noise reduction.

9. The NMR measurement system according to claim 4, wherein the shielding chamber is hinged with an edge of the human-bearing bed surface of the bed body through a hinge structure.

10. The NMR measurement system according to claim 1, wherein the magnet has a single-sided magnet structure, and the single-sided magnet structure has an ergonomic arc surface fitting with a body surface adjacent to a target organ for detection.

* * * * *